United States Patent [19]

Hurst

[11] Patent Number: 4,985,625

[45] Date of Patent: Jan. 15, 1991

[54] TRANSFER LINE FOR MASS SPECTROMETER APPARATUS

[75] Inventor: James Hurst, San Jose, Calif.

[73] Assignee: Finnigan Corporation, San Jose, Calif.

[21] Appl. No.: 120,747

[22] Filed: Nov. 12, 1987

Related U.S. Application Data

[63] Continuation of Ser. No. 836,809, Mar. 6, 1986.

[51] Int. Cl.$^5$ ............................................. H01J 49/04
[52] U.S. Cl. ..................................... 250/288; 250/281
[58] Field of Search .................... 250/288 A, 288, 281, 250/282

[56] References Cited

U.S. PATENT DOCUMENTS 4,298,795 11/1981 Takeuchi et al. ............... 250/288 A Primary Examiner—Jack I. Berman
Attorney, Agent, or Firm—Flehr, Hohbach, Test, Albritton & Herbert

[57] ABSTRACT

A transfer line used between a gas chromatograph and an ion source of a mass spectrometer is constructed with an inner tube, a middle tube and an outer tube. Disposed within the middle tube are a heater unit which extends along the middle tube and a sensor well. The remaining air space in the middle tube is filled with compacted fine thermally conductive powder. Thermal insulation is provided between the middle and outer tubes. End seals are provided to maintain the integrity of the vacuum system of the mass spectrometer.

11 Claims, 2 Drawing Sheets

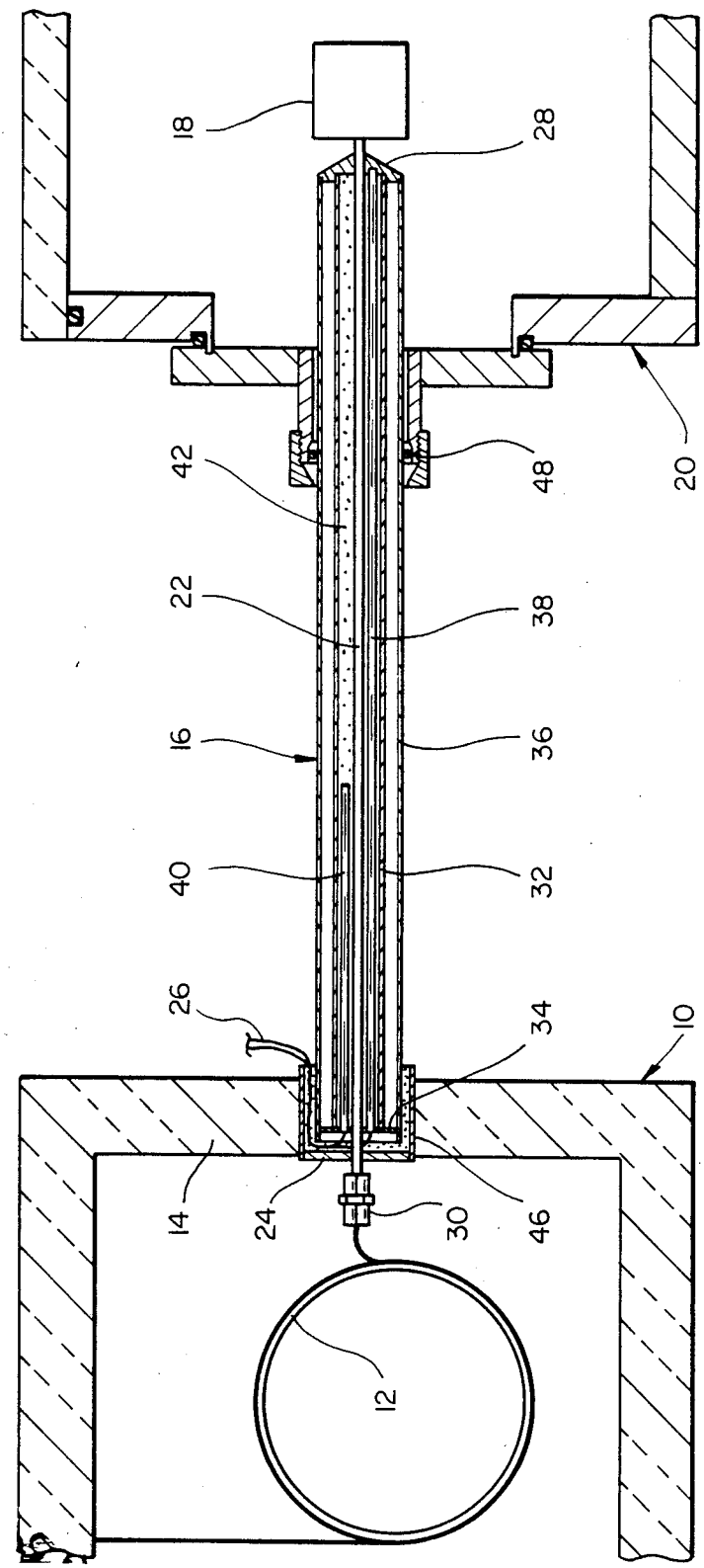
FIG_1

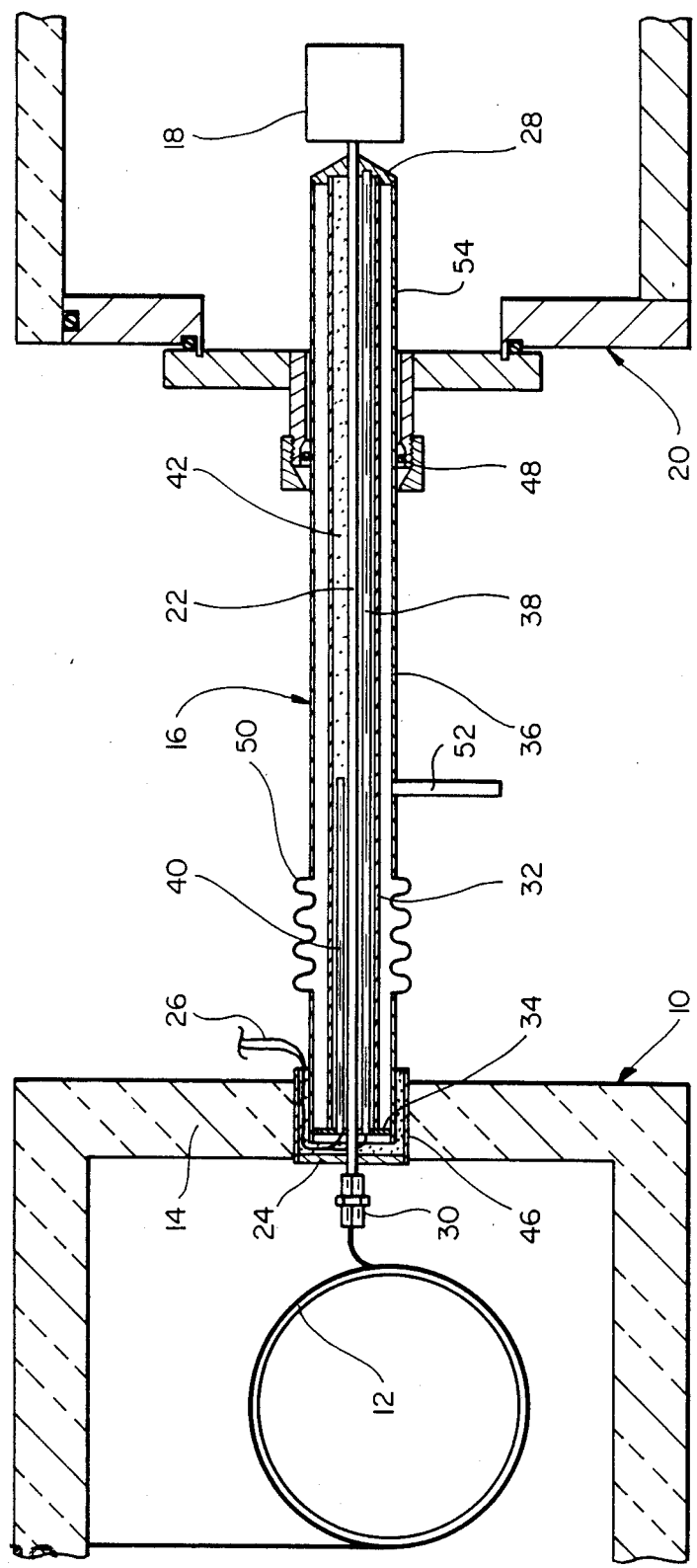
FIG_2

TRANSFER LINE FOR MASS SPECTROMETER APPARATUS

This is a continuation of application Ser. No. 836,809 filed Mar. 6, 1986.

DESCRIPTION

1. Technical Field

This invention relates to a mass spectrometer apparatus and in particular to a transfer line useful with a mass spectrometer and gas chromatograph.

2. Background Art

Mass spectrometers generally include an ion source disposed in a vacuum system for achieving analysis of chemical substances. Samples of chemical substances, which are generally mixtures of compounds, are processed in a gas chromatograph (GC) that separates the mixtures into individual components that can be analyzed in the mass spectrometer (MS). The GC has a tubular column which is heated in the GC oven. The effluent from this column needs to be transferred by means of a transfer line from the GC column, which is typically at atmospheric pressure, to the MS ion source that is held in vacuum. However, during the transfer it is necessary to maintain a uniform temperature across the length of the transfer line. If a significant temperature gradient exists so that the temperature varies at different points along the transfer line, cold spots may occur to cause condensation from the gas phase of the sample so that it will not be passed through to the MS. On the other hand, hot spots that appear will cause compounds to degrade thermally with a resultant change in their chemical structure.

One prior art approach to overcome these problems was to use a flexible transfer line formed of tubing through which the GC column was passed. The tubing was wrapped with heater tape and insulated with various types of insulation. This approach experienced problems, of nonuniformity of, heat distribution, especially at the entrance to the vacuum system and at bends in tube. Also, this particular approach required that the heater tape be wound evenly across the tube, and if the assembly techniques did not achieve uniform windings, thermal differences would be observed. A second prior art approach utilized a box type oven that is constructed around a tube which was heated with rigid block heaters. Ceramic insulation was provided and uniformity of heating was also a problem. Access to vacuum fittings was provided through a removable lid. This type of structure was complex, costly and did not achieve the degree of heating uniformity that is desired.

SUMMARY OF THE INVENTION

An object of this invention is to provide a temperature control for a transfer line disposed between a gas chromatograph and an ion source of a mass spectrometer apparatus.

Another object of this invention is to provide an effective seal of the mass spectrometer against air leaks that would tend to degrade the vacuum, and thereby ensure that only the gas chromatograph effluent will enter the ion source.

Another object is to provide a seal against the ion source to allow pressurization of the ion source.

According to this invention, a transfer line between a gas chromatograph and the ion source of a mass spectrometer apparatus is formed of three tubes, which may be concentric or eccentric relative to each other, or flexible or rigid. The middle tube houses a heater and a sensor well. The heater is disposed along the middle tube and is located adjacent to the inner tube. The sensor well is also disposed within the middle tube adjacent to the inner tube and the heater. The remaining volume within the middle tube is filled with a thermally conductive material. The space between the middle and outer tubes contains air or other insulating material, or is evacuated, and thus serves as an insulating volume. The tubes are appropriately sealed to prevent leakage and to retain the thermally conductive material, as well as the heater and sensor well.

BRIEF DESCRIPTION OF THE DRAWINGS

The invention will be described in detail with reference to the drawing in which:

FIG. 1 is a schematic view of a mass spectrometer system illustrating the novel transfer line used for coupling a gas chromatograph and an ion source, in accordance with this invention; and FIG. 2 is a schematic view of a mass spectrometer system depicting another embodiment of the invention.

DETAILED DESCRIPTION OF THE INVENTION

With reference to FIG. 1, a gas chromatograph (GC) 10 includes a GC column 12 wherein a sample to be analyzed is disposed. The sample generally is a mixture of compounds in a solvent. In order for the mass spectrometer system to be able to analyze the sample, the compound mixture is separated into individual components and transferred by means of a transfer line 16 from the GC column 12, which is at atmospheric or greater pressure, to an ion source 18 located in a vacuum chamber 20.

In accordance with one embodiment of this invention, the transfer line is formed with three longitudinal tubes. The tubes in this instance are made of stainless steel preferably of 304 grade for compatibility with the mass spectrometer structure, However other compatible with operational requirements may be used.

The inner tube 22 has an open end positioned in the GC chamber through which the effluent or eluant from the GC column is passed. The end of the inner tube 22 is welded to an end plate 24 which provides mechanical protection for heater and sensor leads 26 that constitute an auxiliary control for the gas chromatograph. The transfer line may be controlled by any type of temperature controller, including the gas chromatograph. The other end of the inner tube 22 is welded to an end cap 28, and has a radiused end for sealing against the ion source 18. A vacuum fitting 30 is provided with the inner tube at the GC end of the transfer line to seal the GC column into the vacuum system 20.

The middle tube 32 is welded at one end to the end cap 28 and at the other end to a baffle plate 34. The baffle plate provides a partial seal at the GC end of the transfer line 16. The baffle plate minimizes air movement in the annular space between the middle tube 32 and the outer tube 36 so that heat transfer by convention is effectively minimized between the two tubes. The baffle plate also allows differential expansion between the middle and outer tubes. A heater 38 is positioned within the middle tube 32, adjacent to the inner tube 22. The heater extends along the full length of the middle tube 32. In addition, a sensor well 40 is located within the middle tube adjacent to the inner tube and the heater 38. The space within the middle tube that is not occupied by the heater, sensor well and the inner tube is filled with a compacted fine thermally conductive powder 42, which may be made of copper or aluminum by way of example.

The space between the middle tube 32 and the outer tube 36 acts as insulation, thereby limiting heat transfer to the outer tube. The space may contain air or any thermally insulating material to provide the desired limitation on heat transfer.

In another embodiment of the invention, as depicted in FIG. 2, the space between the middle and outer tubes is evacuated to provide the desired insulation. In this implementation, a metal bellows 50 is welded into a portion of the outer tube 36 and the baffle plate 34 is welded to the end of the outer tube 36, so that a sealed annular chamber is formed between the middle and outer tubes This chamber is evacuated of air to reduce or remove the thermal transfer that would occur by conduction or convection between the two tubes. The bellows 50 allows for differential thermal expansion between the middle and outer tubes which are at significantly different temperatures during normal operation.

Evacuation of air can be accomplished by evacuating the sealed annular chamber prior to and during the final welding operation. Welding can be achieved by use of electron beam, laser or other well known techniques which do not degrade the quality of the vacuum. The sealed annular chamber may contain a small amount of getter material to ensure that the vacuum does not degrade with time.

The evacuation of air can also be achieved by attaching an evacuation device 52 to the chamber to run during the time when the transfer line is operational.

An alternative approach for evacuating air from the annular chamber is to connect the chamber to the vacuum chamber 20 forming part of the mass spectrometer vacuum system, as indicated by the opening in the outer tube at the area 54. The end cap 28 also limits heat conduction to the outer tube, thereby restricting the outside temperature of the outer tube to operating limits of the O-ring seal 48 at the transfer line inlet. When the operating temperature is set above 200° C., a heat shield is provided to fit over the transfer line for safety of the operator.

The end of the middle tube 32 is sealed with a high temperature cement that serves to retain the conductive powder, the heater and sensor well. The sensor well has an opening at the end facing the gas chromatograph to allow insertion and removal of a heat sensor device. An inlet sleeve 46 is fitted to the wall of the GC oven 14 to provide protection for the heater and sensor leads 26.

The outer surface of the outer tube 36 is polished to provide a sealing surface for an O-ring type seal 48 located at the entrance to the vacuum system for the ion source. The outer surface of the middle tube 32 and the inner surface of the outer tube 36 are electropolished to reduce emissivity and to increase reflectivity of infrared radiation.

In operation, the transfer line 16 is inserted into the vacuum system through the O-ring inlet seal 48 and is positioned close to the ion source 18. At the gas chromatograph end, the transfer line is inserted into the GC inlet sleeve 46 and into the gas chromatograph structure. The GC column 12 is inserted through a fitting in the gas chromatograph and passed through the inner tube 22 until it protrudes from the end of the transfer line 16 into the ion source 18. The fitting 30 is then tightened in the GC to seal the GC column to the vacuum system. The transfer line is then moved against the ion source 18 to effect a seal between the transfer line and the ion source. The seal 48 is then tightened to seal the transfer line into the vacuum system.

The transfer line 16 is heated uniformly by means of the heater 38 to a predetermined temperature between ambient and 400° C., by way of example, and the temperature is controlled and maintained steady at the predetermined temperature by means of the auxiliary control including the heater and sensor leads 26. Alternatively, the transfer line may be heated at a given rate to match a temperature program of the gas chromatograph. For example, the temperature may be raised at a rate of 20° C. per minute up to 200° C., and at 10° C. per minute from 200 to 350° C.

By virtue of the heater that extends along the length of the middle tube, and the use of the thermally conductive powder, an even temperature distribution along the full length of the transfer line is ensured, thereby precluding deleterious cold spots and hot spots. The simple design of the transfer line allows removal for cleaning or replacement through the same vacuum inlet without the need of special tools.

What is claimed is:

1. A mass spectrometer apparatus having a gas chromatograph including a gas column and an ion source comprising:
   a transfer line coupled between said gas column and said ion source comprising an assembly of coaxial spaced tubes including an inner tube through which the effluent or eluant from the gas column is directly passed to the ion source, a middle tube and an outer tube;
   a heater unit housed within the and extending along the entire length of said middle tube; and thermally conductive material contained between the entire length of said middle tube and the inner tube to fill all of the unoccupied space between the middle tube and inner tube whereby the inner tube is uniformly heated to pass the effluent or eluant from the gas column to the ion source without changing the chemical structure.

2. An apparatus as in claim 1, wherein said tubes are made of stainless steel or other vacuum compatible material.

3. An apparatus as in claim 1, wherein said thermally conductive material is made of a compacted fine copper or aluminum powder.

4. An apparatus as in claim 1, including an end cap joined to one end of each of said tubes.

5. An apparatus as in claim 4, including a baffle plate joined to the other end of said middle tube for minimizing air movement between said middle and outer tubes.

6. An apparatus as in claim 5, including a high temperature cement for sealing said other end to retain said thermally conductive material and said heater unit within said middle tube.

7. An apparatus as in claim 1, wherein the outer surface of said middle tube and the inner surface of said outer tube are electropolished for reducing emissivity and increasing reflectivity of infrared radiation.

8. An apparatus as in claim 1, including a sensor well contained within said middle tube for housing a heat sensor.

9. An apparatus as in claim 1 in which a bellows is formed in said outer tube for forming a sealed annular chamber between said middle tube and said outer tube, and wherein said chamber is evacuated of air.

10. An apparatus as in claim 9, including air evacuation means coupled to said annular chamber.

11. An apparatus as in claim 9, wherein said ion source is disposed within a vacuum chamber and said annular chamber is connected to said vacuum chamber.

* * * * *

UNITED STATES PATENT AND TRADEMARK OFFICE
CERTIFICATE OF CORRECTION

PATENT NO. : 4,985,625

DATED : January 15, 1991

INVENTOR(S) : HURST, James

It is certified that error appears in the above-identified patent and that said Letters Patent is hereby corrected as shown below:

```
Column 2, line 41, after "other" insert --materials--
Column 2, lines 61-62, change "convention" to --convection--
```

Signed and Sealed this

Thirtieth Day of June, 1992

Attest:

DOUGLAS B. COMER

*Attesting Officer*  *Acting Commissioner of Patents and Trademarks*